(12) United States Patent
Cornell et al.

(10) Patent No.: US 6,573,109 B1
(45) Date of Patent: Jun. 3, 2003

(54) SURFACE AMPLIFIER

(75) Inventors: Bruce A. Cornell, Neutral Bay (AU); Ronald J. Pace, Farrer (AU)

(73) Assignees: Australian Membrane and Biotechnology Research Institute, Homebush (AU); The University of Sydney, Sydney (AU)

( * ) Notice: Subject to any disclaimer, the term of this patent is extended or adjusted under 35 U.S.C. 154(b) by 0 days.

(21) Appl. No.: 08/530,370

(22) PCT Filed: Apr. 20, 1994

(86) PCT No.: PCT/AU94/00202

§ 371 (c)(1),
(2), (4) Date: Oct. 10, 1995

(87) PCT Pub. No.: WO94/24562

PCT Pub. Date: Oct. 27, 1994

(30) Foreign Application Priority Data

Apr. 21, 1993 (AU) ............................................... PL8393
Nov. 17, 1993 (AU) ............................................. PM2489
Mar. 8, 1994 (AU) ............................................. PM4302

(51) Int. Cl.[7] ..................... G01N 33/544; G01N 27/26; G01N 33/50
(52) U.S. Cl. ...................... 436/528; 204/403; 204/415; 204/418; 205/778; 205/793; 435/7.1; 435/817
(58) Field of Search ................................. 204/403, 415, 204/418; 205/778, 793; 435/817, 7.1; 436/528

(56) References Cited

U.S. PATENT DOCUMENTS 5,229,302 A * 7/1993 Miyazaki et al. ............ 436/537

FOREIGN PATENT DOCUMENTS

| AU | B 21279/88 | 3/1989 |
| AU | B 40797/89 | 3/1990 |
| AU | B 50334/90 | 8/1990 |
| AU | A 14657/92 | 10/1992 |
| AU | A 51444/93 | 4/1994 |
| EP | 0 261 887 | 3/1988 |

* cited by examiner

Primary Examiner—Rodney P Swartz
(74) Attorney, Agent, or Firm—Nixon & Vanderhye

(57) ABSTRACT

The present invention relates to a membrane for use in detecting the presence of an analyte. The membrane comprises an array of closely packed self-assembling amphiphilic molecules and a plurality of first and second receptor molecules, the first receptor molecules being reactive with one site on the analyte and second receptor molecules being reactive with another site on the analyte. The first receptor molecules are prevented from lateral diffusion within the membrane whilst the second receptor molecules are free to diffuse laterally within the membrane. The membrane is characterized in that the ratio of first receptor molecules to second receptor molecules is 10:1 or greater.

11 Claims, 4 Drawing Sheets

Compound I

Compound IV

Compound II

Compound III

Compound V

Compound VI

SURFACE AMPLIFIER

Figure 1:
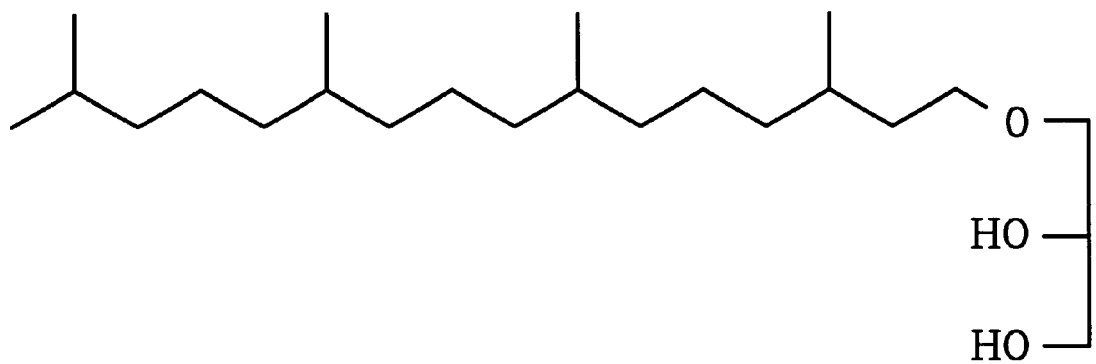

The present invention relates to membranes for use in detecting the presence of an analyte.

BACKGROUND OF THE INVENTION

In International patent application No WO90/08783, it is disclosed how a biosensor of high sensitivity and specificity may be constructed based on a lateral segregation principle incorporating ionophores in a supported bilayer membrane. The preferred embodiment of the invention described in this application included gramicidin as the ionophore, which is known to form a conducting channel only when two monomers, one in each of the two bilayer leaflets, align themselves appropriately to form a bilayer spanning dimer. The monomers in one monolayer (called the "bottom" monolayer) are restrained from lateral mobility by chemical crosslinking in that monolayer, or by attachment through suitable linking groups to an underlying substrate, or by some other means. The monomers in the other (called "top") monolayer are free to diffuse laterally within that monolayer and form conducting channels by alignment with the bottom layer monomers. The top layer monomers have receptor moieties attached, which are accessible to the analyte in the solution phase above the membrane. These receptors may be any of the general types previously described, such as polyclonal or monoclonal antibodies, antibody fragments including at least one Fab fragment, antigens, etc. Another class (called "complementary") of receptor moieties are also attached at the membrane surface. This second class of receptor moieties is restrained from lateral mobility by attachment through to the bottom (immobilised) layer. Detection of analyte occurs when an analyte molecule is bound, at complementary sites on itself, to two receptors of both the mobile and immobilised class. This restrains the gramicidin monomer attached to one receptor from aligning itself with a monomer in the bottom layer, so causing a lowering of membrane electrical conduction which constitutes the detection event.

Such biosensors typically possess comparable surface concentrations of channel attached and immobilised receptor moieties. As such, it is necessary to ensure that all immobilised and mobile receptors are respectively of the same type, as analyte induced cross-linking between mobile channel attached receptors will typically not lead to efficient gating. In addition, the detection sensitivity of such a device in a convenient time (approximately 100 seconds) is set by the known diffusion rate constant, $K_{on}$ (approximately $10^8$ $M^{-1}s^{-1}$) for binding from solution under physiological conditions. In order that a significant (approximately 50%) fraction of detection sites be occupied (here channels to be gated), the analyte concentration, c, must satisfy, $$c > 1/(K_{on} \times 100) \qquad (1)$$

This general requirement limits any detection device, operating under the above requirements, without some additional means of detection amplification and sets an analyte detection concentration limit of approximately $10^{-10}$M.

DESCRIPTION OF THE INVENTION

The present inventors have found that an improvement in sensitivity of membranes for use in detecting the presence of an analyte can be obtained by increasing the ratio of fixed receptor molecules to mobile receptor molecules above a ratio of 1:1.

Accordingly, the present invention consists in a membrane for use in detecting the presence of an analyte, the membrane comprising an array of closely packed self-assembling amphiphilic molecules and a plurality of first and second receptor molecules, the first receptor molecules being reactive with one site on the analyte and second receptor molecules being reactive with another site on the analyte, the first receptor molecules being prevented from lateral diffusion within the membrane whilst the second receptor molecules are free to diffuse laterally within the membrane, the membrane being characterized in that the ratio of first receptor molecules to second receptor molecules is 10:1 or greater.

In a preferred embodiment of the present invention the ratio of first receptor molecules to second receptor molecules is in the range 10:1 to $10^5$:1 and is preferably about 1,000:1.

In yet a further preferred embodiment of the present invention the first and second receptor molecules bind to different epitopes on the analyte.

In a preferred embodiment of the present invention a membrane is a bilayer and includes a plurality of ionophores comprising first half membrane spanning monomers provided in one layer and second half membrane spanning monomers provided in the other layer, the first half membrane spanning monomers being prevented from lateral diffusion within the membrane whilst the second half membrane spanning monomers are free to diffuse laterally within the membrane, the second receptor molecules being bound to the second half membrane spanning monomers such that the binding of the analyte to the first and second receptor molecules causes a change in the conductance of the membrane.

The first and second half membrane spanning monomers may be any such molecules known in the art, however, it is presently preferred that the first and second half membrane spanning monomers are gramicidin or one of its derivatives.

In a further preferred embodiment of the present invention the membrane includes membrane spanning lipids. It is further preferred that the first receptor molecules are attached to the membrane spanning lipids.

The present inventors have also developed a novel method of increasing the number of first receptor molecules by using a loose polymer network attached to the membrane. Accordingly, in another embodiment of the present invention linear polymer chains of radius of gyration of approximately 100 to 300 Å are attached to the surface of the membrane, the first receptor molecules being attached to the linear polymer chains.

The linear polymer chains are preferably attached to the membrane at one or two points through suitably functionalised lipids in the top layer. These may be membrane spanning lipids.

In a preferred embodiment of the present invention the radius of gyration of the linear polymer chains is approximately 200 Å. All antibodies then attached to the polymer chain will be within approximately 500 Å of the surface of the membrane.

It is preferred that the ratio of linear polymer chains to lipids in the membrane is approximately $1:10^4$. This should give "loose contact" packing of the polymer on the surface of the membrane thereby allowing free diffusion of the first half membrane spanning monomers.

The polymer chains are preferably condensed polyethylene glycol.

The radius of gyration, $S_o$ is given by $S_o^2 = \frac{1}{3}\alpha^2 l^2 n$ for a chain containing tetrahedral bonds of length, l, n is the number of links and $\alpha^2$ a constant characteristic or the polymer. For PEO (polyethylene oxide) (—$CH_2$—$CH_2$—O—)$_m$ 1 is the average $CH_2$—$CH_2$ or $CH_2$—O bond length, ~1.5 Å, and $\alpha^2$~2.

n=3 m for PEO (ie ~3 times no. of monomer units).

If $S_o$~200 Å, then n~25,000 (mw~400,000).

The mean mass fraction of polymer in the 500 Å thick layer is $$\sim \frac{4 \times 10^5}{6 \times 10^{23} \times (5 \times 10^{-6})^3} \sim 0.005,$$

i.e. <1%.

This should still permit reasonably easy lateral movement of antibody/ion channel complexes on the surface.

The readily available form of PEO is PEG, polyethyleneglycol. OH—$CH_2$—$CH_2$—($CH_2$—$CH_2$—O) m$CH_2$—$CH_2$—OH. This has hydroxyl groups at each chain end. So a chain with n~25,000 and ~10 functional attachment points for membrane anchoring or antibody binding) might be formed by condensing shorter chained PEG (n~2,500) with a suitably bifunctional (e.g. dicarboxylic acid) molecule containing also a side chain (e.g. hydrazide) for antibody/lipid attachment.

It is envisaged that a common attachment chemistry be used for the antibodies and membrane attachment lipids (e.g. hydrazide linkage to aldehydes). The polymer may be attached first to the membrane surface (by adding it as a ~1% solution in saline) and the unreacted excess removed. Then suitably activated antibody would be added and reacted.

This method of attachment has several potential advantages over that proposed earlier for anchoring proteins directly at the surface through short linkages to membrane spanning lipids.

1) The antibodies now have much greater local freedom to orient for a cross-linking reaction. This should approximate the conditions obtained within an ELISA assay. If the inner layer tethered gramicidin density is no higher than ~1:$10^4$, the statistical gating off of each on analyte induced cross-linking of channel and polymer bound antibodies should still apply. Even with single point attachment of the polymer chains to mobile top layer lipids, the weakly overlapping mass of polymer "spheres" should resist lateral mobility on the hundreds of Å or greater length scale.
2) A substantially higher surface density of "immobilised" antibodies is possible.
3) The loose, "bio compatible" polymer net at the surface will probably reduce non-specific protein binding to the membrane.

In a further preferred embodiment of the present invention the membrane is attached to an electrode via linking molecules such that a space exists between the membrane and the electrode. Preferred linking molecules are those disclosed in application No PCT/AU92/00132 and PCT/AU93/00509. The disclosure of each of these applications is incorporated herein by reference.

The first half membrane spanning monomers may be prevented from diffusing laterally in the membrane using any of a number of known techniques, however, it is presently preferred that the first half membrane spanning monomers are attached to the electrode via linker groups.

In yet a further preferred embodiment of the present invention a fluorescent quencher is attached to the first receptor molecule and a fluorescent species is attached to the second receptor molecule.

In such an arrangement the membrane is illuminated by the exciting wavelength of the fluorescent species. Upon addition of the analyte, the analyte is bound to the receptors. Due to the greater proportion of bound first receptor it is more probable that the analyte will be bound to the first receptor molecule. The mobile receptor diffusing through the membrane will then come into contact with the analyte bound to the first receptor molecule. The second receptor molecule will then bind to the analyte and the fluorescent group will be quenched and the emitted fluorescence will drop. Using this approach the presence of an analyte can be detected by a drop in fluorescence.

As used herein the term "receptor molecule" is used in its widest context. The receptor molecule may be any chemical entity capable of binding to the desired analyte. The receptor molecule is any compound or composition capable of recognizing another molecule. Natural receptors include antibodies, enzymes, lectins, dyes and the like. For example, the receptor for an antigen is an antibody while the receptor for an antibody is either an anti-antibody or preferably, the antigen recognized by that particular antibody.

The first and second receptor molecules may be the same or different and are preferably selected from the group consisting of polyclonal or monoclonal antibodies, fragments thereof including at least one Fab fragment, antigens, lectins, haptens and dyes. It is most preferred that the receptor molecules are antibodies or fragments thereof.

It will be clear to persons skilled in the art that the membrane of the present invention may advantageously incorporate a number of lipid and linker compounds described in PCT/AU93/00509. It is intended that such modifications are within the scope of the present invention and the disclosure of this co-pending application is incorporated herein by reference.

BRIEF DESCRIPTION OF THE DRAWINGS

The present invention will now be described in more detail with reference to the accompanying Example and drawings, in which:

FIG. 1 shows compound I, described below;

FIG. 2 shows compound II, described below;

FIG. 3 shows compound III, described below;

FIG. 4 shows compound IV, described below;

FIG. 5 shows compound V, described below;

FIG. 6 shows compound VI, described below; and

FIG. 7 is a plot of conducting channels before/after gating against tethered mobile receptors.

EXAMPLE

Electrodes:

The following method describes the fabrication of electrodes for use in biosensor applications. The electrode consists of a glass substrate and patterned thin gold film with an adhesion layer of chromium. The counter electrode is applied externally into the biosensor well.

1. Clean microscope glass slides are used (Lomb Scientific cat no. 7101, dimensions 26×76×1.0–1.2 mm) as described below. Powder free plastic gloves are used to handle the slides.
2. All slides are removed from the box in which they are supplied and immersed in a freshly prepared solution of $H_{2O2}$ (1 vol.) and $H_2SO_4$ (3 vol.) for 10 min.
3. All slides are removed from the solution using TEFLON-coated (TEFLON is a trademark for polytetrafluoroethylene tweezers, immersed in deionized water and then rinsed in running deionized water for 10 minutes. Following this they are blown dry with pure nitrogen derived from boil-off from a liquid nitrogen storage tank.

4. The clean slides are not stored but loaded into the evaporation apparatus immediately.
5. The relevant shadow mask for patterning the slides was cleaned by blowing away excess material using the pressurized high purity nitrogen described above.
6. The cleaned glass slides are positioned within the locating grooves on the shadow mask and both mask and slides placed in a high vacuum chamber.
7. The vacuum system is pumped to a pressure of less than $5 \times 10^{-6}$ Torr over a period of approximately 45 minutes.
8. Using an electrical heating element, 99.9% chromium from Balzers, Germany is evaporated from a tungsten container onto the glass surface. The thickness of the film is measured and the deposited layer controlled at 20 nm final thickness deposited at a rate of 0.1–9.3 nm/s.
9. Using a similar but separate tungsten container, isolated from the chromium container via a movable vane, 99.99% gold from Johnson Mathey (Australia) Ltd is evaporated at 0.1 nm/s to a depth of 100 nM.
10. The chamber and the electrodes are permitted to cool for approx. 10 minutes and then brought up to atmospheric pressure by introducing nitrogen gas onto the chamber.
11. Using powder-free gloves once more, the mask containing the clean slides is removed from the chamber and using teflon-coated tweezers the slides are removed form the mask and placed in a storage container or placed directly onto chromium plates brass assemblies.
12. The electrodes placed in storage boxes are further packaged within low volatiles plastic bags following their evacuation and using a heat sealer.
13. Electrodes should be used within 24 hours of their preparation.

Materials and Methods:
1. Using whole gold coated microscope glass slides described above, are taken directly from the evaporator and mounted into a chromium coated brass clamp containing 16 TEFLON wells assembled such that each of the wells forms a sealing contact with the gold surface and permits the retention of approximately 200 $\mu$l of phosphate buffered (pH7.4) saline solution above the gold electrode surface.
2. Prior to the addition of the saline solution a series of ethanolic solutions were added to the well and thus onto the fresh gold surface to form the membrane.
3. During these procedures a face mask is worn to prevent contamination of the fresh gold surface by the operator's breath.
4. The ethanolic solutions are added in two stages, one to form the inner or "bottom" layer of the membrane and the second to form the outer or "top" layer of the membrane.

Figure 4:
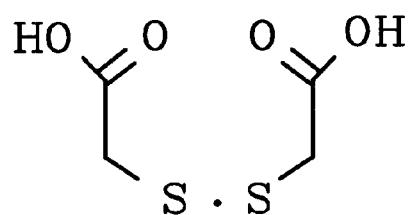
Figure 2:
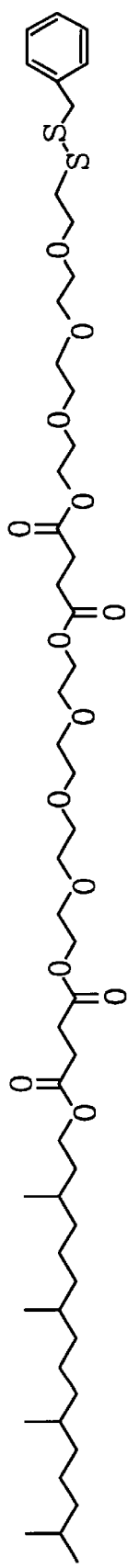
Figure 3:
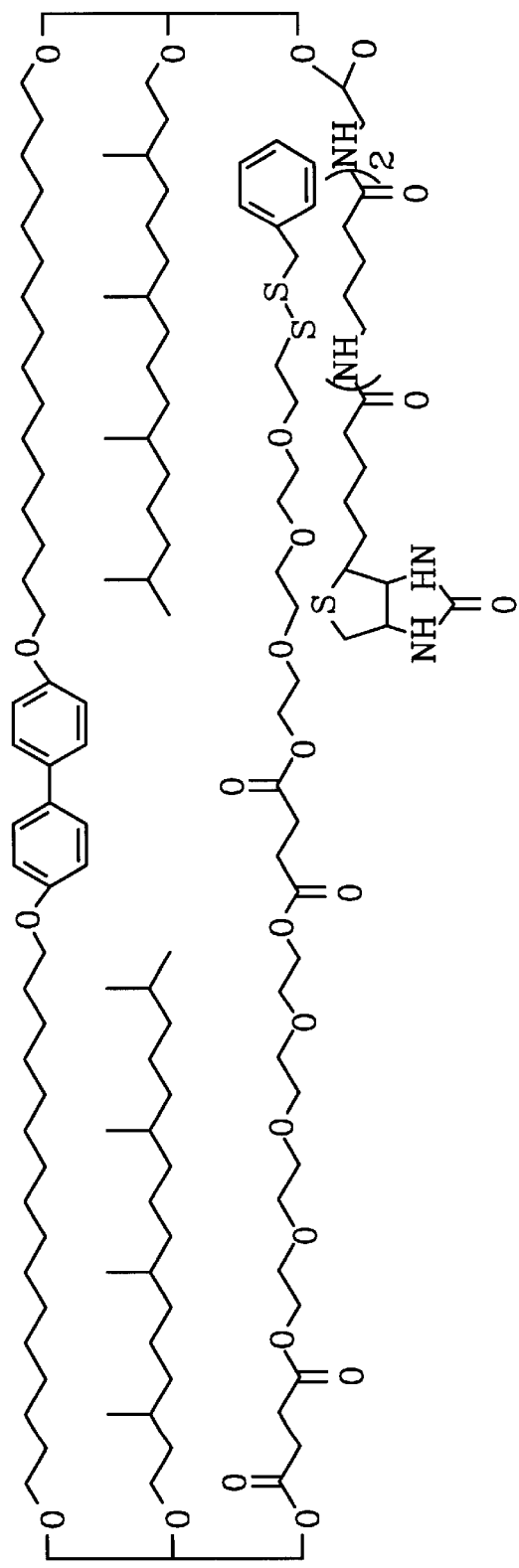
Figure 5:
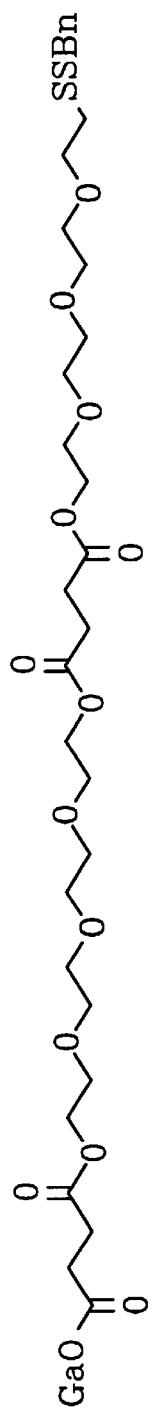

Bottom Layer:
   3 $\mu$l of an ethanolic solution containing:
      10 mM Glycero-mono-phytanyl-ether (GMPE) (the synthesis of this compound is set out in PCT/AU93/00509)
      compound I (shown in FIG. 1) 1 mM di-tetra-ethylene-glycol diphytanyl benzyl disulphide (DLP)
      compound II (shown in FIG. 2) 0.1, 1.0, & 10 $\mu$M membrane spanning lipid linked to biotinylated di-aminocapryl (MSLXXB)
      compound III (shown in FIG. 3) 0.8 mM mercaptoaceticacid disulphide (MAAD)
      compound IV (shown in FIG. 4) 0.1 $\mu$M di-tetraethylene glycol gramicidin benzyl disulphide (GaYYSSBn)
      compound V (shown in FIG. 5)
is added to each well, followed immediately by a further 20 $\mu$l of EtOH. The electrodes and solutions are incubated for 5 minutes, washed twice with distilled AR ethanol and stored at room temperature sealed in parafilm. This storage-period may be minutes to weeks and does not appear to be important.

Figure 6:
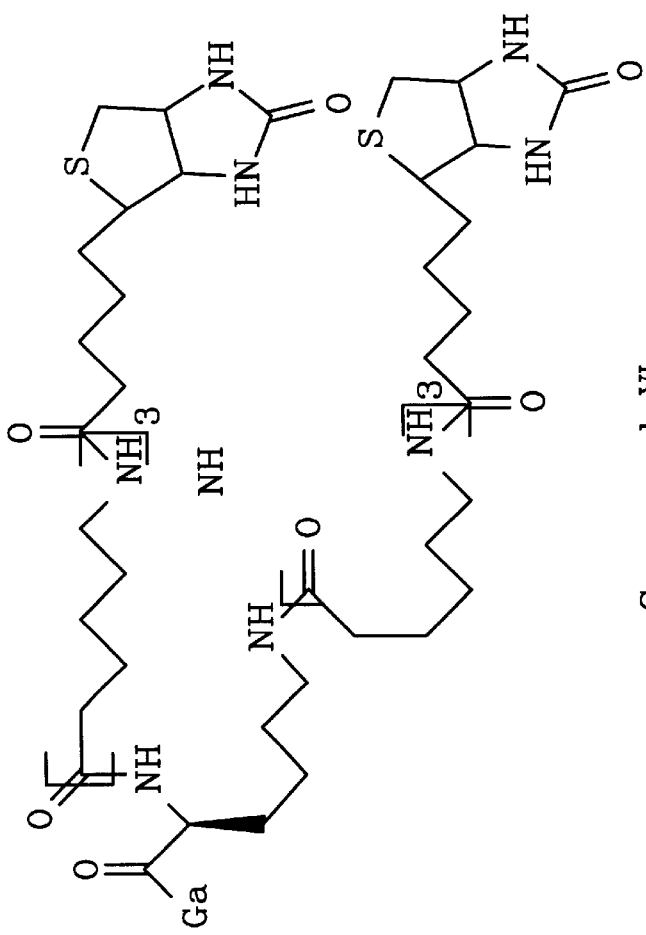

Top Layer:
   Following storage 3 $\mu$l of an ethanolic solution is added containing:
      28 mM GMPE
      0.28 $\mu$M biotinylated bis di-aminocapryl gramicidin (Ga6X)
      compound VI (shown in FIG. 6)

The electrodes are then rinsed twice with 500 $\mu$l 0.1N phosphate buffered saline pH7.4, 5 mM $PO_4^+$, from a 500 $\mu$l glass $\mu$l syringe and the impedance of the membrane formed by this process measured relative to a silver wire in contact with the saline solution within the 200 $\mu$l well above the electrode.

Impedance Measurements:

The impedance is measured using an a.c. excitation potential of 10–100 mv at a series of frequencies from 1000 Hz to 0.1 Hz. The impedance spectrum derived from these measurements are interpreted in terms of both:
   the resistive element in an equivalent electrical circuit comprising a capacitor depicting the membrane, in parallel with a resistor depicting the ion channels both of these being in series with a capacitor depicting the Helmholtz capacitance of the electrode.
   the phase angle between the applied potential and the resultant current flow through the membrane passing between the gold electrode and the reference electrode. The aspect of the phase measurement employed in tis context is the frequency, ($f_{min}$), at which a phase minima occurs denoting the frequency at which the membrane is most resistive and thus dominated in its impedance by the conducting ion channels.

Experimental:

Impedance measurements were made at 23° C. on groups of x4 wells, in blocks of 16 sharing a common gold electrode. The assembled blocks contained the above range of tethered receptors (MSLXXB) for a fixed concentration of mobile receptors (Ga6XB).

The ratio of tethered/mobile receptors shown in the accompanying graph was from 0–1000. This ratio may be calculated from the ratio of [DLP]/[MSLXXB] of:
   1 mM DLP to 10 $\mu$M MSLXXB; or 1 mM DLP to 1 $\mu$M MSLXXB; or 1 mM
   DLP to 0.1 $\mu$M MSLXXB; or 1 mM DLP to 0 $\mu$M MSLXXB, giving number ratios of 100, 1000, 10,000 & infinity,
   assuming that the solution concentrations of these species translate into the number ratios on the gold surface. Although some quantitative differences may exist between the solution and surface values, the qualitative trend is evident in FIG. 7.

Figure 7:
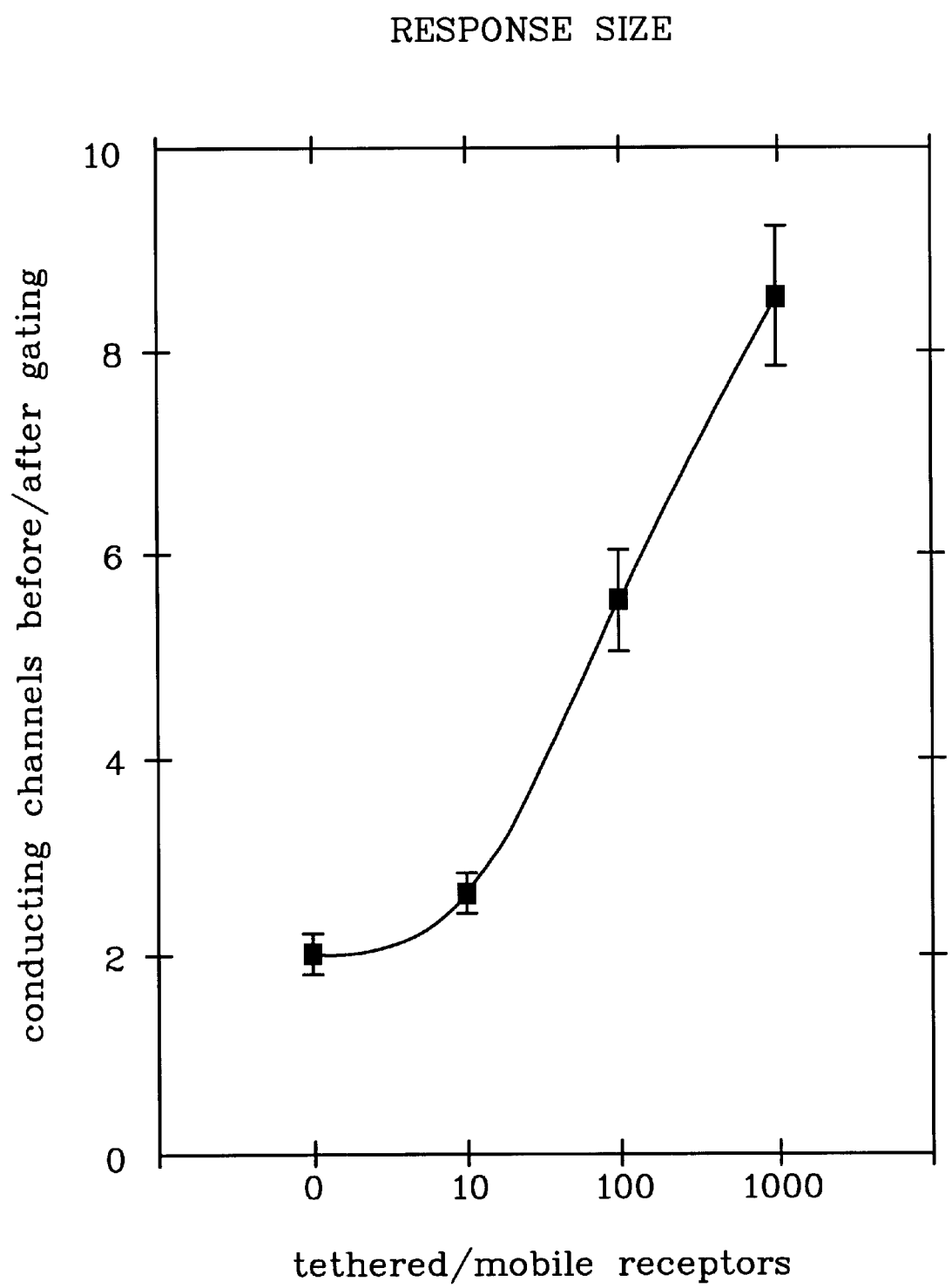

From the number ratios of tethered receptors, and the known concentration of top layer mobile receptors, (1:100,000 relative to GMPE), the ratio of tethered/mobile receptors may be estimated as: 1000, 100, 10 & 0 respectively. The ratio of the number of conducting channels before and after gating is shown in FIG. 7 as a function of the ratio of tethered/mobile receptors.

Gating was achieved by the addition of 2 $\mu$l of 0.01 mg/ml streptavidin directly into each well. Following the addition, the frequency, ($f_{min}$), at which the phase minimum occurred was observed, and the gating ratio determined by dividing the $f_{min}$ prior to gating by $f_{min}$ after gating was complete.

Advantages of Increased Ratios of Tethered/mobile Species

Increasing the tethered/mobile receptor ratio causes an increase in the ratio of the channels conducting before and after challenge with the streptavidin. This arises due to the greater number of tethered receptors causing a more effective cross-linking and disruption of the ion channels and thus a more sensitive response to the analyte.

This means the detection sensitivity of the device increases with the tethered/mobile receptor ratio, as the minimum reliable detectable change in the conducting channel population (about 10%) is achieved with smaller analyte concentrations.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A membrane for use in detecting the presence of an analyte, the membrane comprising an array of closely packed self-assembling amphiphilic molecules and a plurality of first and second receptor molecules, the first receptor molecules being reactive with one site on the analyte and second receptor molecules being reactive with another site on the analyte, the first receptor molecules being prevented from lateral diffusion within the membrane whilst the second receptor molecules are free to diffuse laterally within the membrane, the membrane being characterized in that the ratio of first receptor molecules to second receptor molecules is 10:1 or greater.

2. A membrane as claimed in claim 1 in which the ratio of first receptor molecules to second receptor molecules is in the range 10:1 to $10^5$:1.

3. A membrane as claimed in claim 2 in which the ratio of first receptor molecules to second receptor molecules is about 1,000:1.

4. A membrane as claimed in claim 1 in which the first and second receptor molecules bind to different epitopes on the analyte.

5. A membrane as claimed in claim 1 in which the membrane is a bilayer and includes a plurality of ionophores comprising first half membrane spanning monomers provided in one layer and second half membrane spanning monomers provided in the other layer, the first half membrane spanning monomers being prevented from lateral diffusion within the membrane whilst the second half membrane spanning monomers are free to diffuse laterally within the membrane, the second receptor molecules being bound to the second half membrane spanning monomers such that the binding of the analyte to the first and second receptor molecules causes a change in the conductance of the membrane.

6. A membrane as claimed in claim 1 in which the membrane includes membrane spanning lipids.

7. A membrane as claimed in claim 6 in which the first receptor molecule is attached to the membrane spanning lipid.

8. A membrane as claimed in claim 1 in which linear polymer chains of radius of gyration of approximately 100 to approximately 300 Å are attached to a surface of the membrane, the first receptor molecules being attached to the linear polymer chains.

9. A membrane as claimed in claim 4 in which the first and second half membrane spanning monomers are gramicidin or derivatives thereof.

10. A membrane as claimed in claim 1 in which the membrane is attached to an electrode via linking molecules such that a space exists between the membrane and the electrode.

11. A membrane as claimed in claim 1 in which a fluorescent quencher is attached to the first receptor molecule and a fluorescent species is attached to the second receptor molecule.

* * * * *